(12) United States Patent
Warner

(10) Patent No.: US 7,625,208 B2
(45) Date of Patent: *Dec. 1, 2009

(54) UNIVERSAL-CONTROL MECHANISM FOR DENTAL IMPLEMENTS

(76) Inventor: Thomas P. Warner, 3704 Meriweather La., Rochester Hills, MI (US) 48306

( * ) Notice: Subject to any disclaimer, the term of this patent is extended or adjusted under 35 U.S.C. 154(b) by 1544 days.

This patent is subject to a terminal disclaimer.

(21) Appl. No.: 10/464,369

(22) Filed: Jun. 17, 2003

(65) Prior Publication Data

US 2003/0232305 A1 Dec. 18, 2003

Related U.S. Application Data

(60) Provisional application No. 60/389,229, filed on Jun. 17, 2002.

(51) Int. Cl.
*A61C 1/02* (2006.01)
*H01H 3/14* (2006.01)

(52) U.S. Cl. .......................... 433/101; 433/98; 200/86.5

(58) Field of Classification Search ................. 433/101, 433/98–99; 606/34; 200/86.5
See application file for complete search history.

(56) References Cited

U.S. PATENT DOCUMENTS

| | | | |
|---|---|---|---|
| 3,742,167 A | 6/1973 | Muther | 200/86.5 |
| 3,809,454 A | 5/1974 | Brambring | 350/84 |
| 3,980,848 A | 9/1976 | Schulz et al. | 200/86.5 |
| 3,980,849 A | 9/1976 | Straihammer | 200/86.5 |
| 3,983,344 A | 9/1976 | Straihammer | 200/86.5 |
| 4,041,609 A | 8/1977 | Bresnahan et al. | 32/22 |
| 4,114,275 A | 9/1978 | Jones et al. | 32/22 |
| 4,156,187 A * | 5/1979 | Murry et al. | 324/142 |
| 4,180,812 A | 12/1979 | Kaltenbach et al. | 340/706 |
| 4,354,838 A | 10/1982 | Hoyer et al. | 433/101 |
| 4,383,167 A | 5/1983 | Gmeinder et al. | 377/2 |
| 4,417,875 A | 11/1983 | Matsui | 433/101 |
| 4,523,911 A | 6/1985 | Braetsch et al. | 433/101 |
| 4,571,681 A * | 2/1986 | Beier et al. | 433/181 |
| 4,798,535 A | 1/1989 | Nielsen | 433/101 |

(Continued)

FOREIGN PATENT DOCUMENTS

WO PCT/US2003/39870 12/2003

OTHER PUBLICATIONS

*Wireless Digital Footswitch*, Dental Products Report, Sep. 2003.

(Continued)

Primary Examiner—John J Wilson

(57) ABSTRACT

A universal-control mechanism for automated selection and control of operation of components within an operatory includes at least one implement, wherein the implement has been assigned a signal address. The mechanism also includes a control device adapted to be activated by a user of the mechanism and to control the operation of the implement. The mechanism also includes a selector switch used to designate the implement selected and a signal generator adapted to receive a signal from the control device when the control device is activated and to generate a command signal directed to the signal address for the implement selected by the selector switch. The mechanism also includes at least one receiver unit operatively connected to the selected implement such that activation of the control device acts to control the implement via the signal generator and the receiver unit to control the operation of the implement.

18 Claims, 4 Drawing Sheets

U.S. PATENT DOCUMENTS

| | | | |
|---|---|---|---|
| 4,837,857 A | 6/1989 | Scheller et al. | 455/617 |
| 4,983,901 A | 1/1991 | Lehmer | 318/685 |
| 5,249,121 A | 9/1993 | Baum et al. | 364/413.01 |
| 5,355,804 A * | 10/1994 | Garcia et al. | 104/93 |
| 5,408,284 A * | 4/1995 | Berger et al. | 353/103 |
| 5,422,521 A | 6/1995 | Neer et al. | 307/119 |
| 5,423,231 A | 6/1995 | Helfrich et al. | 74/561 |
| 5,554,894 A | 9/1996 | Sepielli | 307/119 |
| 5,580,347 A | 12/1996 | Reimels | 604/30 |
| 5,635,777 A | 6/1997 | Telymonde et al. | 307/119 |
| 5,712,460 A | 1/1998 | Carr et al. | 200/86.5 |
| 5,883,615 A | 3/1999 | Fago et al. | 345/156 |
| 5,931,669 A | 8/1999 | Fornoff et al. | 433/28 |
| 5,970,457 A * | 10/1999 | Brant et al. | 704/275 |
| 6,017,354 A * | 1/2000 | Culp et al. | 606/170 |
| 6,074,388 A | 6/2000 | Tockweiler et al. | 606/34 |
| 6,179,829 B1 | 1/2001 | Bisch et al. | 606/1 |
| 2003/0004497 A1 | 1/2003 | Chappuis | 606/1 |
| 2004/0115591 A1 | 6/2004 | Warner | 433/98 |
| 2005/0130097 A1 | 6/2005 | Warner | 433/101 |
| 2005/0130098 A1 | 6/2005 | Warner | 433/101 |

OTHER PUBLICATIONS

*Wireless Wonders: Bear Foot Pedal's Foot Control*, Dental Products Report, Dec. 2001.

Schleyer, Titus K.L., D.M.D., Ph.D, et al., *The Technologically Well-Equipped Dental Office*, The Journal of the American Dental Association, vol. 134, Jan. 2003, pp. 30-41.

PCT Search Report, PCT/US2003/39870, mailing date Mar. 28, 2005.

* cited by examiner

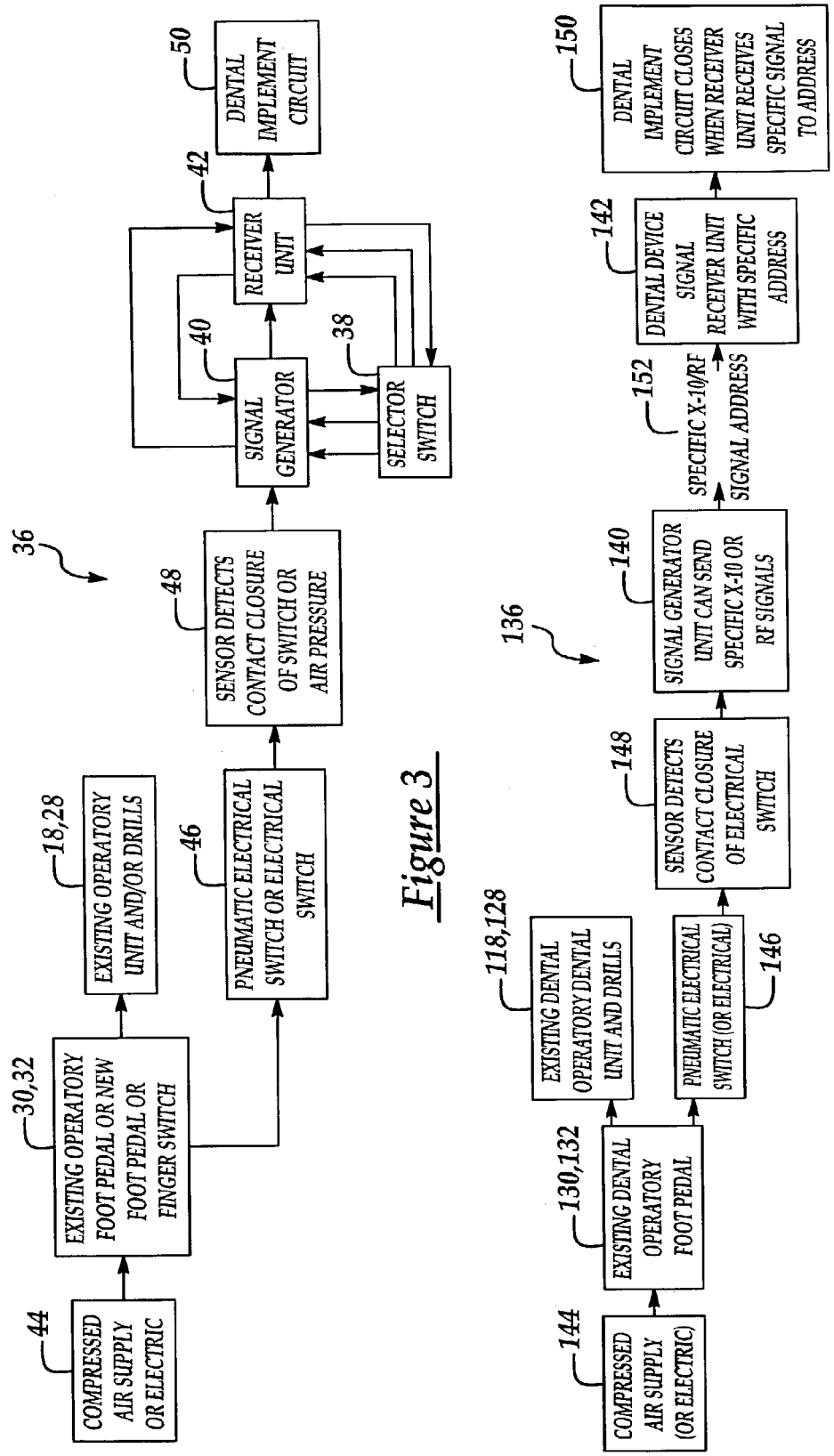

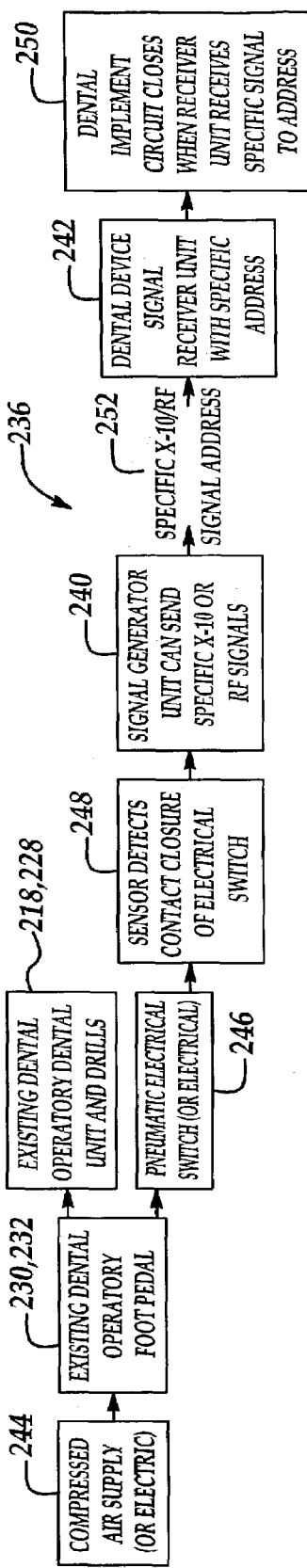
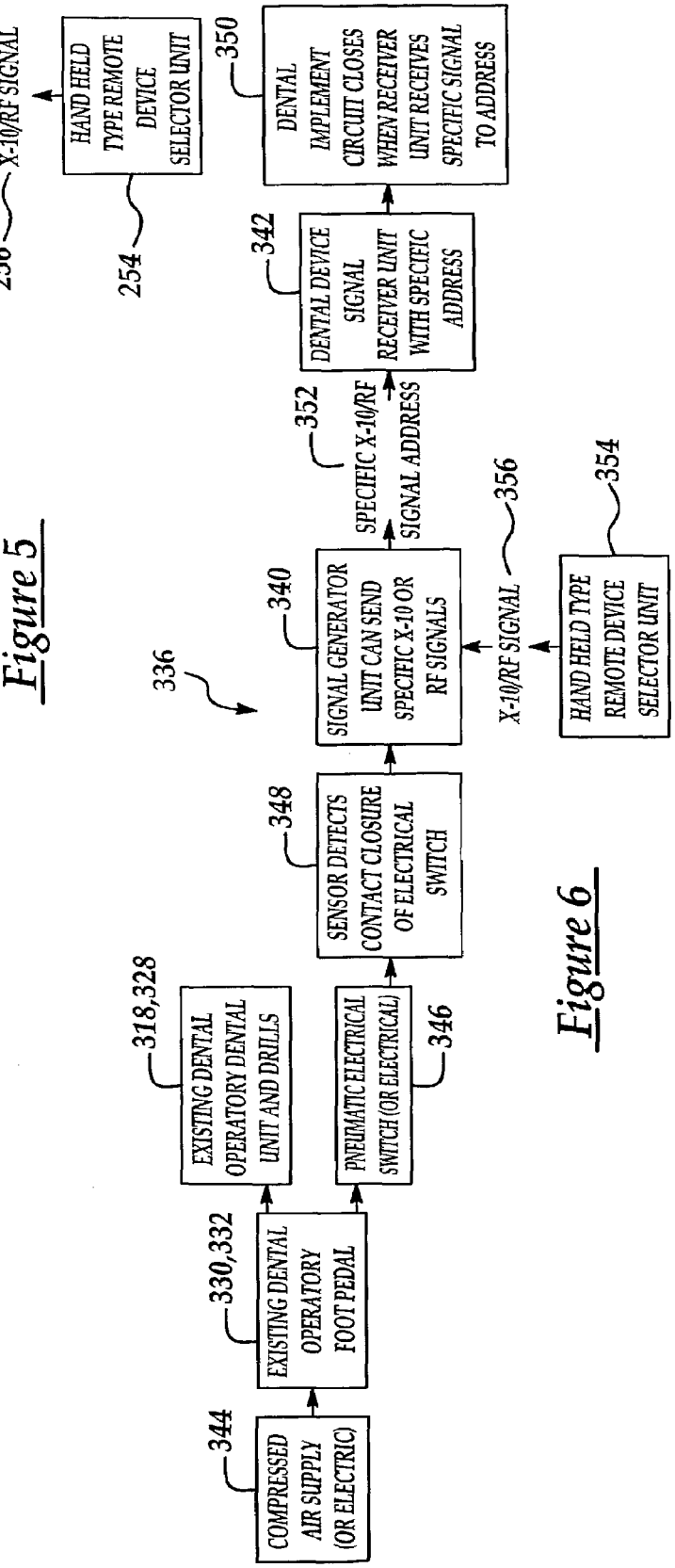
Figure 5
Figure 6

UNIVERSAL-CONTROL MECHANISM FOR DENTAL IMPLEMENTS

CROSS-REFERENCE TO A RELATED APPLICATION

This application claims the benefit of U.S. Provisional Application No. 60/389,229 filed Jun. 17, 2002 and entitled "Universal-Control Mechanism for Dental Implements."

BACKGROUND OF THE INVENTION

1. Field of the Invention

The present invention relates, generally, to a control mechanism that is adapted for use in a dental operatory and, more particularly, to a control mechanism that may be used to universally select and control the operation of each of a variety of dental implements of the operatory.

2. Description of the Related Art

In the practice of dentistry, the implements, tools, and related equipment required to competently perform dentistry are generally located in an operatory, examining, or hygiene room. A typical dentist's office has more than one operatory. Standard features of an operatory configuration may include a treatment chair, a treatment console, a side console, a hand-piece delivery system, a dental and x-ray view box, a cart, a dentist's chair, an assistant's chair, an insert-storage unit, and/or an equipment turntable.

The treatment chair typically is located in a central area of the operatory and associated with a dental unit, which will be described in greater detail below. The treatment console often is mounted to a wall of the operatory and features a working-surface area for both the dentist and an assistant to help simplify procedural setups. The treatment console also can house a computer for efficiently and conveniently integrating patient-record keeping into the operatory or for viewing by a patient. The treatment chair can also feature a monitor and keyboard for such purposes. The side console usually provides the operatory with a built-in sink, a writing surface, and storage space for back-up materials and instruments and emergency supplies. The hand-piece delivery system can be mounted to the treatment chair and integrated with the dental unit and a cuspidor, for instance. The dental and x-ray view box can be integrated with the delivery system. The cart provides flexible instrument positioning, a mobile working-surface area for procedural setups, and convenient storage. The insert-storage unit can be built into a wall of the operatory to hide an x-ray machine and allow it to be shared between two adjacent operatories. The equipment turntable is used to support video- or intra-oral-camera equipment and other equipment. Patients, dentists, assistants, and staff members can enter and exit the operatory from a doorway located typically at the rear of the operatory.

The operatory may further include an extended floor box located, for instance, at the foot of the treatment chair. The floor box is usually designed to house compressed air, a vacuum source, and/or a waste-water disposal system. The operatory may also include a self-contained water system and an internal umbilical to clean-up operatory floor space.

The various components of the dental system just described can be configured with respect to each other and within the operatory in many ways. However, those having ordinary skill in the art will appreciate from the description that follows that the dental equipment described above and the location of an opening for ingress into and egress from the operatory forms no part of the present invention and is described here merely to facilitate understanding of the invention. In any event, it can easily be seen that the standard operatory contains a complex dental system having many components, some of which are large. Furthermore, although the complete dental system strives to maximize floor space, flexibility, and cleanliness of the operatory, many operatories have limited floor space and, thus, can become complicated with all of the equipment necessary to carry out the sophisticated procedures common to modern dentistry.

Making the dental system more complex and, hence, the operatory even more complicated, the dental unit supports instrumentation—particularly, a number of hand-held dental implements or tools that may be operatively connected to the delivery system. Familiar examples of such implements are lasers, air-abrasion units, electro-surgery units, cavitron and piezo-ultrasonic units, prophy jets, diamond probes, wands, intraoral-video devices, water-pick devices, syringes, electrically or air-powered drills, and water irrigators. The use of these implements requires skillful and careful attention to detail. As such, it is imperative to have precise control to perform intricate procedures with them and cause no harm to a patient.

It is very common in the practice of dentistry to have many of these implements stored or supported in the central dental unit that may be associated with the treatment chair. Alternatively, since these implements can be expensive, such that there is often an advantage in sharing them among operatories, many implements may be stored or supported on the portable dental carts that may be moved from operatory to operatory. The placement of the carts within an operatory varies, depending upon the preference of the operator. On the other hand, many implements may be stored or supported even on the consoles or in cabinets of the consoles associated with each operatory. Some implements are even permanently incorporated safely into an operatory, but this is done at a considerable expense. Further, permanent incorporation limits the placement of the implements within the operatory and inhibits sharing of the implements among operatories.

Dental implements are usually electrically powered, but may also be pneumatically powered, and controlled by the dental professional during use. Specifically, the implements can be supported in association with pivoting arms mounted to the treatment chair so that the dental team, in either a left- or right-hand configuration, can easily position the implements precisely where they are needed. From there, speed regulation and "on/off" control of the dental implements are often required. As such, it is also common to have mechanical, electrical, or pneumatic trigger-circuits and a power source or main compressor associated with the implements such that when each implement is lifted from a respective holder, the implement is automatically coupled to an appropriate utility supply for powering the implement. In fact, the carts generally need access to a 120-V outlet since almost all the implements operate on 120 V.

Dental professionals must have the ability to control the functions of the implement as well as selectively shift, switch, or vary among at least some of the functions thereof. In addition, dental professionals must have the ability to selectively shift, switch, or vary among at least some of the implements. Moreover, many dental procedures may require extremely precise control of the dental implements. If an implement is controlled by a finger-activated switch, the tactile sensitivity of the operator of the implement could be compromised. Therefore, attempting to control the implement with the same hand that is simultaneously manipulating the implement to perform a delicate procedure is a difficult skill to master and is generally not preferred.

Accordingly, a control mechanism, such as a foot pedal, is frequently provided for each implement, thereby freeing the hands of the dental professional so that he or she can concentrate on the procedure at hand. A foot pedal is utilized to, for example, control the speed of operation of the implement. Thus, each of the implements noted above typically includes a foot pedal associated with it. Each pedal is operatively connected to a cable or conduit that is ideally routed within the operatory to be non-intrusive. The pedal is usually placed at any convenient location on the floor of the operatory next to the treatment chair containing a patient. The pedal is used to control the respective implement, leaving the hands of the dentist or other dental professional treating the patient free for treatment of the patient. Often, a plurality of pedals are provided in accordance with the number of implements to be operated.

Conventional foot pedals or control devices commonly known in the related art are often "directly acting" in that switches are activated in the pedal to turn "on" and "off" the implements. Thus, conventional pedals can be cumbersome devices that include switches and associated electrical conduits. Furthermore, cables, conduits, cords, tubing, wire, and the like extend to and from the pedals across the floor of the operatory and present a trip hazard and, consequently, a major safety issue for patients and dental professionals alike.

Accordingly, dental professionals have found multiple pedals and their associated conduits and cords to be burdensome and a hindrance to the operators' mobility due to the size, bulk, quantity, etc. of the pedals and their associated conduits and cords. The pedals have proven to be too numerous, inconvenient, cumbersome, and otherwise unsatisfactory in terms of their operation and utility.

More particularly, the pedals create messy and dangerous clutter and, therefore, a possible safety hazard within the limited space of the modern operatory. Also, positioning of the dental unit can be dictated by the positioning of the various pedals and, thus, results in inefficient use of the operatory. In addition, since pedals are not standardized, each pedal often has a different level of control, feel, and location than the other pedals such that the operator of the pedals fails to achieve or loses a consistent level of control among the implements and precise feel for the pedals. Additional pedals cause confusion and increase the risk of inadvertent activation of the pedals, possibly causing harm to the patient, the operator, or a staff member. Furthermore, when an implement needs to be moved, either within the operatory or among operatories, an asepsis problem occurs. Specifically, the operatory floor and, as a result, the pedal or cable associated with it may not be sufficiently clean such that when the implement is moved with the pedal, the pedal may contaminate the implement.

In response to these problems of the related art, multi-functional foot controls have been developed in an attempt to put an end to dangerous wires running all over the floor of an operatory and to carry out all the important dental functions in a hands-free manner without diverting the operator's attention from performing these functions. However, these foot controls suffer from many disadvantages. In particular, some of these foot controls are hard-wired and contain a multitude of individual foot-activated pedals, thus causing confusion as to which pedal to use at a given time. Furthermore, multi-functional foot pedals of the type known in the related art cannot be used among operatories. Other foot controls—which are radio-frequency ("RF") activated and, therefore, wireless—only function in conjunction with a separate computer to capture, for example, digital-radiograph images and intraoral-camera/-video images. However, these devices are controlled by separate "RF" compatible pedals and, therefore, do not mitigate the problem of using numerous foot-pedal controls to operate the various dental implements in an operatory.

Thus, there is a need in the related art for a control mechanism that can be used to universally control each of a multitude of implements employed within a dental operatory. Furthermore, there is a need in the related art also for a universal foot-operated control mechanism. More specifically, there is a need in the related art for a universal foot-operated control mechanism that does not require the use of a multitude of pedals; can be used among operatories; does not require a separate computer to function; does more than just capture images; and can be employed with existing operatory foot pedals.

SUMMARY OF THE INVENTION

The invention overcomes the disadvantages in the related art in a universal-control mechanism for automated selection and control of operation of components within an operatory. The mechanism includes at least one implement, wherein the implement has been assigned a signal address. The mechanism also includes a control device adapted to be activated by a user of the mechanism and to control the operation of the implement. The mechanism also includes a selector switch used to designate the implement selected and a signal generator adapted to receive a signal from the control device when the control device is activated and to generate a command signal directed to the implement selected by the selector switch. Alternatively, the signal generator can send a common signal, but the selector switch controls which implement receives that signal. The mechanism also includes at least one receiver unit operatively connected to the selected implement such that activation of the control device acts to control the implement via the signal generator and the receiver unit to control the operation of the implement.

Accordingly, a primary object of the present invention is to provide a convenient, reliable, and structurally simple apparatus for controlling each of a multitude of dental implements of a dental unit within a dental operatory.

One advantage of the present invention is that it allows consolidation of functions and integration of control of many dental implements in connection with one convenient control device, such as a single foot pedal controller.

Another advantage of the present invention is that it enhances the simplicity of the configuration of the operatory and saves valuable operatory floor space by integrating functions often controlled by respective separate pedals.

Another advantage of the present invention is that it allows the dental practitioner to easily operate many functions and efficiently utilize an open-floor plan (thus, saving enough space to fit other options into the operatory), helps to keep the operatory floor uncluttered and to maximize the use of precious floor space, enhances the openness of the operatory, makes it easier to conduct dentistry, and allows patients to easily enter and exit the operatory.

Another advantage of the present invention is that it provides flexible delivery of instrumentation without compromising any functionality and further enhances a clean, professional look of the operatory.

Another advantage of the present invention is that it can eliminate the asepsis problem associated with moving implements.

Another advantage of the present invention is that it helps to increase efficiency, reduce operator fatigue, and provide an unobstructed field of control over each of the dental implements employed in the operatory.

Another advantage of the present invention is that it allows a consistent level of control of all implements operating therefrom.

Another advantage of the present invention is that it eliminates the hazards of additional pedals and their associated cables.

Another advantage of the present invention is that it allows for maximum flexibility in the placement of implements within an operatory.

Another advantage of the present invention is that it allows sharing of implements among operatories in an efficient manner.

Another advantage of the present invention is that it does not require a multitude of foot-actuated buttons or pedals on a single device to control a like multitude of implements, but rather only one foot-actuated button, hand-operated or voice-actuated control.

Still another advantage of the present invention is that it does not require a separate computer to function, but can be integrated with a computer and voice-activation software.

Other objects, features, and advantages of the present invention will be readily appreciated as the same becomes better understood after reading the subsequent description taken in conjunction with the accompanying drawings.

BRIEF DESCRIPTION OF THE DRAWINGS

FIG. 3 is a schematic diagram depicting the general operation of the universal-control mechanism of the present invention.

FIG. 4 is a schematic diagram depicting the command flow circuit of a first alternate embodiment of the universal-control mechanism for dental instruments of the present invention.

FIG. 5 is a schematic diagram depicting the command flow circuit of a second alternate embodiment of the universal-control mechanism of the present invention.

FIG. 6 is a schematic diagram depicting the command flow circuit of a third alternate embodiment of the universal-control mechanism of the present invention.

DETAILED DESCRIPTION OF THE INVENTION

Figure 1:
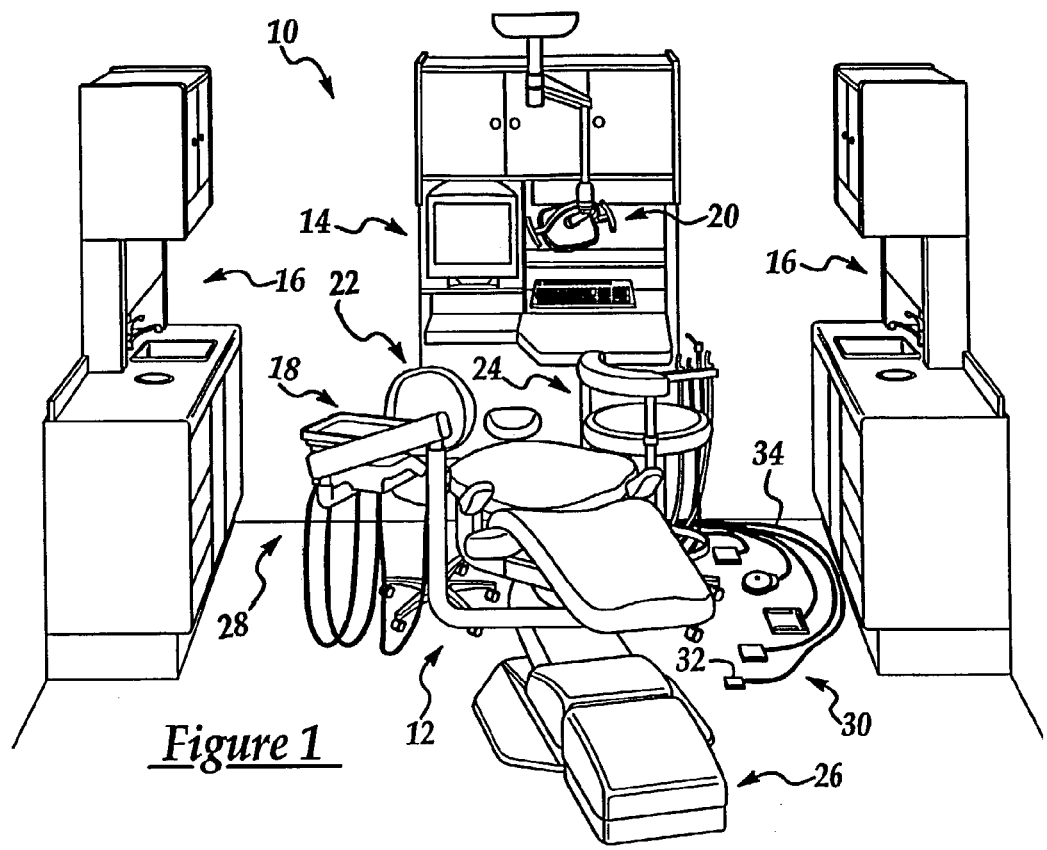
FIG. 1 is an environmental view of a typical dental operatory of the type known in the related art having multiple foot-operated control mechanisms that are used to control the various dental instruments of the related art.
Figure 2:
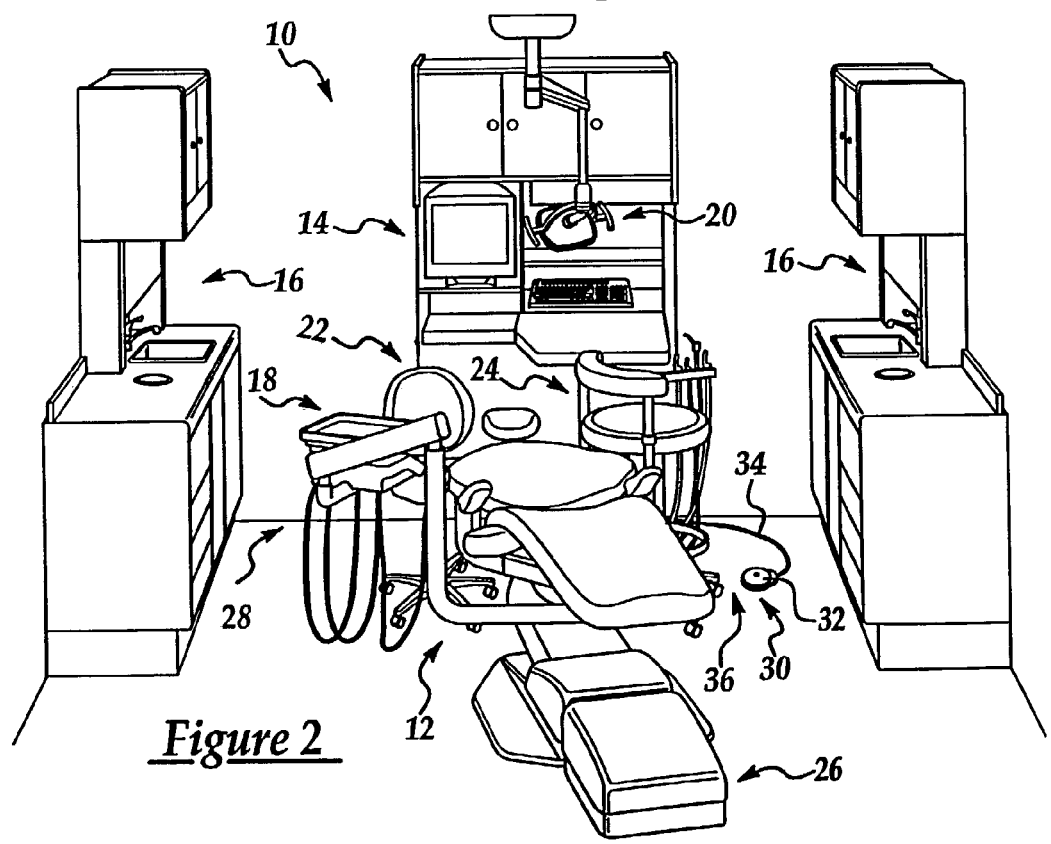
FIG. 2 is an environmental view of a dental operatory having a control mechanism that may be used to control the various dental instruments when used in connection with the universal-control mechanism of the present invention.

Referring now to the figures, where like numerals are used to designate like structure, a dental operatory is generally indicated at 10 in FIGS. 1 and 2. The operatory 10, by and large, includes a treatment chair, generally indicated at 12; a treatment console, generally indicated at 14 and two side consoles, generally indicated at 16. A hand-piece delivery system, or, a dental unit of the type commonly employed in such dental operatories is generally indicated at 18. Similarly, a dental and/or x-ray light is generally indicated at 20 and a dentist's chair is generally indicated at 22. In the representative illustration of FIG. 1, an assistant's chair is generally indicated at 24 and an extended floor box is generally indicated at 26. The operatory 10 also includes a plurality of hand-held dental implements, generally indicated at 28, that are associated with the dental unit 18 adjacent the assistant's chair 24. Those having ordinary skill in the art will appreciate, however, that the operatory 10 shown in FIG. 1 is illustrative of a typical system only and that the operatory 10 can include more or fewer components. For example, other dental systems may also include a mobile cabinet and/or mobile cart, the top of each of which provides a working surface.

As can easily be seen in the operatory 10 shown in FIG. 1, many foot-operated control devices, generally indicated at 30, including pedals 32 and cords 34 operatively connected to the pedals 32 are spread out over a portion of the floor of the operatory 10. Each pedal 32 is associated with an implement 28 or other component of the operatory 10 that may be used by a dental professional in the practice of dentistry.

FIG. 2 illustrates an operatory incorporating a universal-control mechanism for dental implements of the present invention, generally indicated at 36. The universal-control mechanism 36 may employ any suitable control device 30 such as a hand-operated throttle or voice-activated system. Thus, from the description that follows, those having ordinary skill in the art will appreciate that there are a number of different types of control devices 30 that can be employed with the universal-control mechanism 36 of the present invention. However, for purposes of description only and not by way of limitation, the universal control mechanism 36 illustrated in FIG. 2 will be described in connection with the use of a foot-operated pedal 32. A power supply 44, that may include a source of AC electrical power or source of pneumatic pressure, is provided to the operatory as is commonly known in the art. In any event, the universal-control mechanism 36 may be used to universally select and control the operation of a variety of implements 28, as will be appreciated from the description that follows.

Referring now to FIG. 3, the universal-control mechanism 36 generally includes at least one implement 28, wherein the implement 28 has been assigned a signal address. However, those having ordinary skill in the art will appreciate that the universal-control mechanism 36 may be employed in connection with a plurality of implements 28 all of which may be assigned a signal address for a purpose that will be explained in greater detail below. The control device 30 is adapted to be activated by a user of the mechanism 36 and to control the operation of the implement 28. A selector switch 38 is used to designate the implement 28 selected. A signal generator 40 is adapted to receive a signal from the control device 30 when the control device 30 is activated. The signal generator 40 then generates a command signal directed to the implement 28 selected as indicated by the selector switch 38. Alternatively, the signal generator 40 can send a common signal, but the selector switch 38 controls which implement 28 receives that signal. The mechanism 36 also includes at least one receiver unit 42 operatively connected to the selected implement 28 such that activation of the control device 30 acts to control the implement 28 via the signal generator 40 and the receiver unit 42 to control the operation of the implement 28.

In one possible embodiment of the present invention as illustrated in the schematic diagram of FIG. 3, compressed air, generally indicated at 44, is supplied to the foot pedal 32, which is operatively connected to a dental unit 18 and, ultimately, to certain dental implements 28, such as drills and the like. A pneumatically actuated electrical switch 46 is operatively connected to the foot pedal 32. The pneumatically actuated electrical switch 46 closes in response to receipt of compressed air delivered through the line when the foot pedal 32 is depressed. In turn, the pneumatically actuated electrical switch 46 is operatively connected to communicate with the signal generator 40. Thus, when the foot pedal 32 is depressed, the signal generator 40 receives a signal from the pneumatically actuated electrical switch 46. In response to this signal, the signal generator 40 generates a predetermined signal having an "address" that is associated with each individual implement 28 that may be employed in any given operatory. The signal generated is determined by a command provided by the selector switch 38 which is pre-set by the operator.

More specifically, "addresses" (for instance, A1, A2, A3 . . . ) are created for the receiver unit 42 in connection with the implements 28 using, for example, a code dial of the selector switch 38 that is set by a user of the mechanism 36 to the "addresses." Each implement 28 is identified with an "address" that may be different than that of each of the other implements 28. The receiver unit 42 can hold 256 different addresses, for instance. The signal generator 40, which is electrically connected to at least one sensor, such as an electrical switch 48, is capable of sending the different "addresses," or signals, to the implements 28 via the receiver unit 42. The receiver unit 42 can be electrically or pneumatically, for example, connected to the selected implement 28.

The user selects the implement 28 by operating the selector switch 38. The signal generator 40 is then operable to send to the receiver unit 42 a specially coded, low-voltage signal that matches the address of the implement 28 when the pedal 32 is depressed. The signal may be sent via existing AC-power lines using "X-10" technology or using analog or digital radio frequencies. The implement 28 responds to depression and release by the user of the pedal 32 by turning "on" and "off" via the signal generator 40.

In particular, the signal generator 40 generates a signal to be directed to one of the addresses "A1," "A2," "A3" . . . . The signal is identified by the position of the selector switch 38. An "X-10" or "RF" signal is generated and permits the "A1" signal to be directed to an "A1" foot-pedal circuit 50. The signal is then detected by the receiver unit 42 for the implement 28, and implement having address "A1" is activated. This process can be repeated for any of addresses "A2," "A3," "A4" . . . "P16" associated with the various implements 28 used in any given dental operatory.

FIGS. 4 through 7 use flow diagrams to illustrate the steps in a sequence of operations of each of various embodiments of the universal-control mechanism 36. Referring now to FIG. 4, where like numerals increased by 100 are used to designate operations like those of FIG. 3, the steps in a sequence of operations of a first embodiment of a universal-control mechanism for dental implements of the present invention are generally indicated at 136. The steps illustrate a possible basic structure and functional method of the mechanism 136 using a specific signal address 152 sent directly from a signal generator 140 to a receiver unit 142.

More specifically, a compressed-air or electrical supply 144 is directed to a foot pedal 132, which is directed to an existing dental unit 18 having corresponding drills 128 etc. In addition, the foot pedal 132 is operatively connected to a pneumatic or electrical switch 146, which is directed to a sensor 148 that detects contact closure of the pneumatic or electrical switch 146. The sensor 148 is directed to the signal generator 140. The signal generator 140 sends a specific "X-10" or "RF" signal 152 to the receiver unit 142 with the specific address to close a dental implement circuit 150 when the receiver unit 142 receives the specific signal 152 to the address. Alternatively, the signal generator 140 can send a common signal, but the selector switch 138 controls which implement 128 receives that signal. The dental implement circuit 150 is a circuit that resides on each dental implement 128 that responds to signals generated by the universal-control mechanism 136 of the present invention. The mechanism 136 allows the implements 128 to be positioned anywhere within an operatory and shared among operatories.

Referring now to FIG. 5, where like numerals increased by 200 are used to designate operations like those of FIG. 3, the steps in a sequence of operations of a second embodiment of a universal-control mechanism for dental implements of the present invention are generally indicated at 236. The steps illustrate a possible basic structure and functional method of the mechanism 236 using a remote implement selector 254 to send a specific signal address 256.

More specifically, a compressed-air or electrical supply 244 is directed to a foot pedal 232, which is directed to an existing dental unit 218 having corresponding drills 228 etc. In addition, the foot pedal 232 is operatively connected to a pneumatic or electrical switch 246, which is directed to a sensor 248 that detects contact closure of the pneumatic or electrical switch 246. The sensor 248 is directed to a signal generator 240. The signal generator 240 sends a specific "X-10" or "RF" signal 252 or a signal address to a receiver unit 242 with the specific address to close a dental implement circuit 250 when the receiver unit 242 receives the specific signal 252 to the address. Alternatively, the signal generator 240 can send a common signal, but the selector switch 238 controls which implement 228 receives that signal. The dental implement circuit 250 is a circuit that resides on each dental implement 228 that responds to signals generated by the universal-control mechanism 236 of the present invention. In addition, in the embodiment illustrated in FIG. 5, the handheld type, remote selector switch 254 may be employed to select the specific implement 228 via an "X-10"/"RF" signal 256 that allows the dental implement circuit 250 to close when receiving signal 252. The mechanism 236 allows the implements 228 to be positioned anywhere within an operatory and shared among operatories by deactivating the signal generator 240 in unused operatories.

Referring now to FIG. 6, where like numerals increased by 300 are used to designate operations like those of FIG. 3, the steps in a sequence of operations of a third embodiment of a universal-control mechanism for dental implements of the present invention are generally indicated at 336. The steps illustrate another possible basic structure and functional method of the mechanism 336 using a remote implement selector 354 to send a specific signal address 356.

More specifically, a compressed-air or electrical supply 344 is directed to a foot pedal 332, which is directed to an existing dental unit 318 having corresponding drills 328 etc. In addition, the foot pedal 332 is operatively connected to a pneumatic or electrical switch 346, which is directed to a sensor 348 that detects contact closure of the pneumatic or electrical switch 346. The sensor 348 is directed to a signal generator 340 that can send specific "X-10" or "RF" signals 352 as noted above. In addition, in the embodiment illustrated in FIG. 6, the hand-held type, remote selector switch 354 also is used to select via an "X-10"/"RF" signal 356 the specific implement 328 that will receive signal 352. The signal generator 340 sends a specific "X-10" or "RF" signal 352 or a signal address to a receiver unit 342 with the specific address to close a dental implement circuit 350 when the receiver unit 342 receives the specific signal 352 to the address. Alternatively, the signal generator 340 can send a common signal, but the selector switch 338 controls which implement 328 receives that signal. The dental implement circuit 350 is a circuit that resides on each dental implement 328 that responds to signals generated by the universal-control mechanism 336 of the present invention. The mechanism 336 allows for implements 328 to be positioned anywhere within an operatory and shared among operatories.

Figure 7:
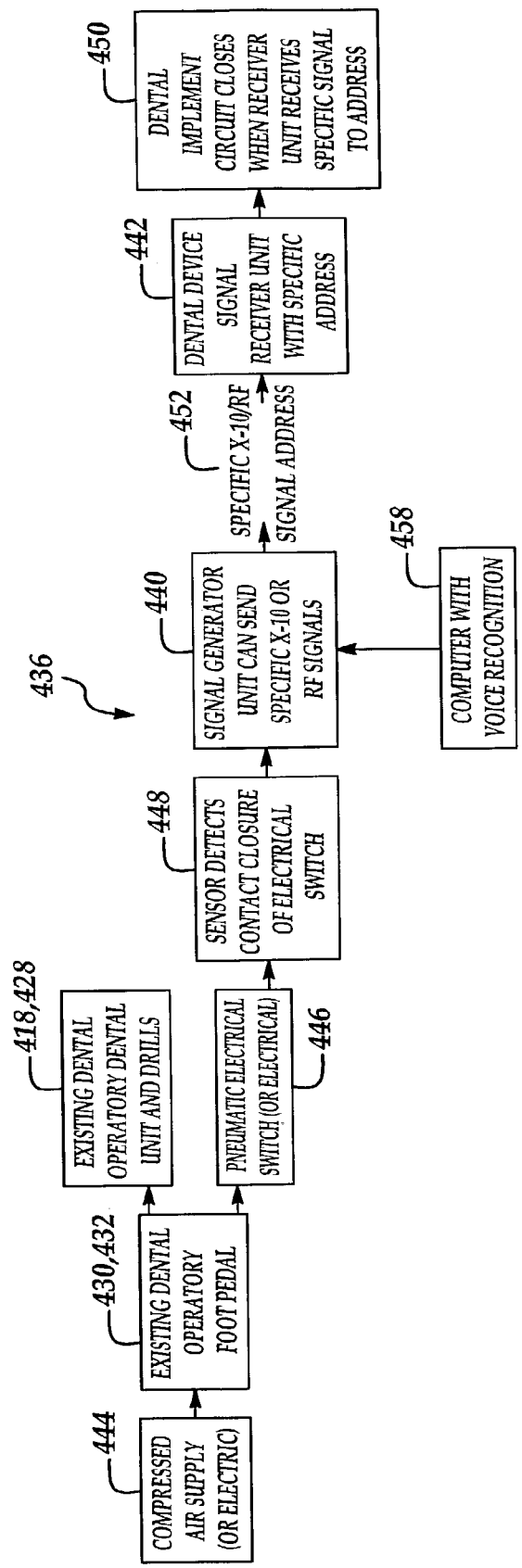
FIG. 7 is a schematic diagram depicting the command flow circuit of a fourth alternate embodiment of the universal-control mechanism of the present invention.

Referring now to FIG. 7, where like numerals increased by 400 are used to designate operations like those of FIG. 3, the steps in a sequence of operations of a fourth embodiment of a universal-control mechanism for dental implements of the present invention are generally indicated at 436. The steps illustrate a possible basic structure and functional method of the mechanism 336 that employs voice-recognition capabilities.

More specifically, a compressed-air or electrical supply 444 is directed to a foot pedal 432, which is directed to an existing dental unit 418 having corresponding drills 428 etc. In addition, the foot pedal 432 is operatively connected to a pneumatic or electrical switch 446, which is directed to a sensor 448 that detects contact closure of the pneumatic or electrical switch 446. The sensor 448 is directed to a signal generator 440 that can send specific "X-10" or "RF" signals 452 to implements 428 as selected by a selector switch operated by voice-activation. Thus, the operator may give the verbal command "camera" to select the camera 428, for example. A receiver unit 442 is operatively connected to the selected implement 428 such that activation of the voice-recognition-operated selector switch acts to designate the selected implement 428 via the signal generator 440, or the receiver unit 442, to control operation of the selected implement 428.

The signal generator 440 sends a specific "X-10" or "RF" signal 452 to the receiver unit 442 with the specific address to close a dental implement circuit 450 when the control device 432 is activated. The dental implement circuit 450 is a circuit that resides on each dental implement 428 that responds to signals generated by the universal-control mechanism 436 of the present invention via the receiver unit 442.

In each of the various embodiments of the universal-control mechanism 36, 136, 236, 336, 436, the receiver unit 42, 142, 242, 342, 442 activates the dental implement circuit 50, 150, 250, 350, 450 when, through the signal generator 40, 140, 240, 340, 440, the receiver unit 42, 142, 242, 342, 442 receives an appropriately addressed "on" signal or data (or an appropriately incrementing or varying signal rate or data) from an existing foot pedal 32, 132, 232, 332, 432, a new foot pedal 32, 132, 232, 332, 432, a finger switch 30, 130, 230, 330, 430, or any other control device 30, 130, 230, 330, 430. The receiver unit 42, 142, 242, 342, 442 also activates when it receives a "safety" signal or data from the selector switch 38, 138, 238, 338, 438, the signal generator 40, 140, 240, 340, 440, or any other designated device and then receives an appropriate signal or data through the signal generator 40, 140, 240, 340, 440 from the control device 30, 130, 230, 330, 430. The receiver unit 42, 142, 242, 342, 442 also may activate when it receives a confirmed "handshake," a "handshake" signal, or a signal or data from the control device 30, 130, 230, 330, 430, an appropriate signal or data through the signal generator 40, 140, 240, 340, 440 from the control device 30, 130, 230, 330, 430.

There are a number of safety features that may be incorporated into the universal-control mechanism 36, 136, 236, 336, 436 of the present invention. For example, the receiver unit 42, 142, 242, 342, 442 will deactivate the foot-pedal circuit 50, 150, 250, 350, 450 when the receiver unit 42, 142, 242, 342, 442 receives either an appropriate addressed "off" signal or data from the signal generator 40, 140, 240, 340, 440 (addressed "off"), the selector switch 38, 138, 238, 338, 438 (all units "off"), or any other designated device (emergency "off") or when the receiver unit 42, 142, 242, 342, 442 has stopped receiving a continuous appropriately addressed signal or data or an appropriately addressed signal or data within a defined amount of time, in terms of milliseconds, for example.

The receiver unit 42, 142, 242, 342, 442 may "reset" itself (become unselected) when power has been terminated to either the implement 28, 128, 228, 328, 428 or the receiver unit 42, 142, 242, 342, 442. For example, the receiver unit 42, 142, 242, 342, 442 may reset itself to prevent accidental activation when moving implements 28, 128, 228, 328, 428 from operatory to operatory. Any desired implement 28, 128, 228, 328, 428 would then have to be reselected by the selector switch 38, 138, 238, 338, 438. The receiver unit 42, 142, 242, 342, 442 may also "reset" itself when an appropriate signal or data has not been received within a defined amount of time in terms of minutes, for example. This feature acts to prevent accidental activation of the implement 28, 128, 228, 328, 428. In order to actuate this implement 28, 128, 228, 328, 428, it would then have to be reselected by the selector switch 38, 138, 238, 338, 438. The receiver unit 42, 142, 242, 342, 442 also may "reset" itself when it receives an appropriately addressed signal or data from a second selector switch 38, 138, 238, 338, 438 or signal generator 40, 140, 240, 340, 440 without terminating power from the previous signal generator 40, 140, 240, 340, 440 or selector switch 38, 138, 238, 338, 438 that has generated the previous appropriate signal. Thus, the receiver unit 42, 142, 242, 342, 442 or implement 28, 128, 228, 328, 428 is turned "off" or reset to prevent accidental activation of the implement 28, 128, 228, 328, 428 by a second operator who selects the same implement 28, 128, 228, 328, 428.

The receiver unit 42, 142, 242, 342, 442 may be connected to the implement 28, 128, 228, 328, 428 internally by an OEM or an after-market installer or externally by splicing into existing foot-pedal wire or tubing or using a patch cord with an appropriate terminating connector. The receiver unit 42, 142, 242, 342, 442 may be powered by 110 V or 220 V, a transformer, or a battery. Each power source may be incorporated into the implement 28, 128, 228, 328, 428 or receiver unit 42, 142, 242, 342, 442 or external to the implement 28, 128, 228, 328, 428 or receiver unit 42, 142, 242, 342, 442. The receiver unit 42, 142, 242, 342, 442 may activate the foot-pedal circuit 50, 150, 250, 350, 450 by acting as an electrical relay, a potentiometer, or an electrical/pneumatic relay or switching system, such as the "wand." Furthermore, the receiver unit 42, 142, 242, 342, 442 may receive "X-I0," "RF," "IR"-wireless, or combined-wire-and-wireless signals. In addition, the receiver unit 42, 142, 242, 342, 442 may control dental, medical, or industrial implements 28, 128, 228, 328, 428 or any switching circuit of any implement 28, 128, 228, 328, 428.

The receiver unit 42, 142, 242, 342, 442 may have a switch or be programmable to allow the receiver unit 42, 142, 242, 342, 442 to be defined as operatory- or operatories-specific and/or unit- or signal-generator specific. This allows the implement 28, 128, 228, 328, 428 to be shared between operatories if so desired. Also, the receiver unit 42, 142, 242, 342, 442 may have a display (such as an LED or LCD) or lights to indicate that the associated implement 28, 128, 228, 328, 428 for the receiver unit 42, 142, 242, 342, 442 has been selected by the selector switch 38, 138, 238, 338, 438, the receiver unit 42, 142, 242, 342, 442 is "on," the receiver unit 42, 142, 242, 342, 442 has received the appropriate safety signal or "handshake" signal (from the selector switch 38, 138, 238, 338, 438 or signal generator 40, 140, 240, 340, 440), and/or the operatory switch is currently in "safety mode" or "handshake mode" with the receiver unit 42, 142, 242, 342, 442.

Finally, the receiver unit 42, 142, 242, 342, 442 may have a timer to allow a specified implement 28, 128, 228, 328, 428 to remain "on" for a predetermined amount of time after the appropriate signal has been terminated. This would allow for air-abrasion-suction units to continue the suction function when the air-abrasion unit has terminated, but residual air pressure still forces air-abrasion particles out the air-abrasion unit (and, hence, the need for suction to continue).

In each of the various embodiments of the universal-control mechanism 36, 136, 236, 336, 436, the selector switch 38, 138, 238, 338, 438 selects the implement(s) 28, 128, 228, 328, 428 that will be activated and thus, by exclusion, the ones that are not to be activated by sending an appropriate "selection" (or "non-selection") signal(s) to the signal generator 40, 140, 240, 340, 440, the receiver unit 42, 142, 242, 342, 442, or both. Also, the selector switch 38, 138, 238, 338, 438 may send wired and/or wireless signals via "X-10," "RF," "IR," or a combination thereof. The selector switch 38, 138, 238, 338, 438 may be physically incorporated into the signal generator 40, 140, 240, 340, 440 or receiver unit 42, 142, 242, 342, 442; fixed mounted, portable, or both. Alternatively, the selector switch 38, 138, 238, 338, 438 may be incorporated into voice-recognition software 58, 158, 258, 358, 458, a microprocessor, or a computer. The selector switch 38, 138, 238, 338, 438 may be programmable to allow it to be operatory- or operatories-specific, signal-generator or signal-generators specific, or receiver-unit or receiver-units specific. The selector switch 38, 138, 238, 338, 438 may also receive a safety or "handshake" signal from the signal generator 40, 140, 240, 340, 440, the receiver unit 42, 142, 242, 342, 442, and/or any other selector switch 38, 138, 238, 338, 438 and have the ability to send an "emergency off" signal to the signal generator 40, 140, 240, 340, 440 and/or the receiver unit 42, 142, 242, 342, 442.

In each of the various embodiments of the universal-control mechanism 36, 136, 236, 336, 436, the signal generator 40, 140, 240, 340, 440 receives a signal or data from the selector switch 38, 138, 238, 338, 438, which dictates the signal to be generated to control the desired implement 28, 128, 228, 328, 428 via the receiver unit 42, 142, 242, 342, 442. Also, the signal generator 40, 140, 240, 340, 440 may receive and/or generate a wired or wireless signal or data via "X-10," "RF," "IR," or a combination thereof. The signal generator 40, 140, 240, 340, 440 will generate an appropriate signal or data for the designated receiver unit 42, 142, 242, 342, 442 when it receives a signal or data from the control device 30, 130, 230, 330, 430. Furthermore, the signal generator 40, 140, 240, 340, 440 may receive a "handshake," confirmation, or security signal or data from the receiver unit 42, 142, 242, 342, 442; send a "handshake," confirmation, or security signal or data to the selector switch 38, 138, 238, 338, 438 and/or receiver unit 42, 142, 242, 342, 442; or send a continuous signal or data to the receiver unit 42, 142, 242, 342, 442 or generate single commands. In addition, the signal generator 40, 140, 240, 340, 440 may have a timing feature that will reset or not allow a signal or data to be generated if the signal generator 40, 140, 240, 340, 440 has not received input within a defined amount of time from the control device 30, 130, 230, 330, 430.

The signal generator 40, 140, 240, 340, 440 may include an "emergency off" or "all receiver units off" feature that generates the appropriate signals or data to terminate control of the receiver unit 42, 142, 242, 342, 442 when the appropriate signal or data has been received from the control device 30, 130, 230, 330, 430 or the selector switch 38, 138, 238, 338, 438. Also, the signal generator 40, 140, 240, 340, 440 may be physically connected to the selector switch 38, 138, 238, 338, 438 and powered by battery, 110 V, or low voltage. Finally, input may be a simple contact closure and open contact or data from the control device 30, 130, 230, 330, 430.

As can easily be seen, the universal-control mechanism 36, 136, 236, 336, 436 for dental implements allows consolidation of functions and integration of control of the many dental implements 28, 128, 228, 328, 428 into the one convenient control device 30, 130, 230, 330, 430 such as a pedal 32, 132, 232, 332, 432, hand-operated control 30, 130, 230, 330, 430 or via voice activation 58, 158, 258, 358, 458. The mechanism 36, 136, 236, 336, 436 enhances the simplicity of the configuration of the operatory and saves valuable operatory floor space by consolidating functions often controlled by respective separate pedals 32, 132, 232, 332, 432. The mechanism 36, 136, 236, 336, 436 allows the dental practitioner to easily operate many functions and efficiently utilize an open-floor plan (thus, saving enough space to fit other options into the operatory), helps keep the operatory floor uncluttered and maximize the use of precious floor space, enhances the openness of the operatory, makes it easier to conduct dentistry, and allows patients to easily enter and exit the operatory. The mechanism 36, 136, 236, 336, 436 provides flexible doctor's and assistant's instrumentation delivery without compromising any functionality and further enhances a clean, professional look of the operatory. The clean-looking, open operatory layout can eliminate the asepsis problem associated with moving implements 28, 128, 228, 328, 428. The mechanism 36, 136, 236, 336, 436 helps to increase efficiency, reduce operator fatigue, and provide an unobstructed field of control over the pedal 32, 132, 232, 332, 432. With the compact mechanism 36, 136, 236, 336, 436, the control devices 30, 130, 230, 330, 430 are out of the way and out of view during patient entry and exit. The mechanism 36, 136, 236, 336, 436 allows consistent level of control of all the implements 28, 128, 228, 328, 428 operating therefrom, eliminates the hazards of additional pedals 32, 132, 232, 332, 432 and their associated cables, and allows for maximum flexibility in the placement of the implements 28, 128, 228, 328, 428 within the operatory and sharing of the implements 28, 128, 228, 328, 428 among operatories. Further, the mechanism 36, 136, 236, 336, 436 does not require a multitude of pedals 32, 132, 232, 332, 432; can be used among operatories; does not require a separate computer to function, but can be integrated with a computer and voice-activation software 58, 158, 258, 358, 458; and can be incorporated into a single preexisting pedal 32, 132, 232, 332, 432.

Those having ordinary skill in the art will appreciate that, although the universal-control mechanism 36, 136, 236, 336, 436 for dental implements 28, 128, 228, 328, 428 is described above in connection with safe, clean use and control of dental implements 28, 128, 228, 328, 428, the mechanism 36, 136, 236, 336, 436 also has other medical and industrial applications as well. To exemplify, the mechanism 36, 136, 236, 336, 436 can be used to operate lights, a stereo, a television, blinds, and a hot-tub jet, just to name a few uses.

The present invention has been described in an illustrative manner. It is to be understood that the terminology that has been used is intended to be in the nature of words of description rather than of limitation. Many modifications and variations of the present invention are possible in light of the above teachings. Therefore, within the scope of the appended claims, the present invention may be practiced other than as specifically described.

What is claimed is:

1. A system for remotely controlling at least one device, comprising:
an RF signal generator configured to transmit a first RF signal when a foot-operated pedal is activated and a first device is selected, the first RF signal having a first address value associated with the first device, the RF signal generator further configured to transmit a second RF signal when the foot-operated pedal is activated and a second device is selected, the second RF signal includes a second address value associated with the second device; and
a first RF receiver unit configured to receive the first RF signal and to actuate the first device when the first RF signal has the first address value.

2. The system of claim 1, further comprising a second RF receiver unit configured to receive the second RF signal and to actuate the second device when the second RF signal has the second address value.

3. The system of claim 1, further comprising:
an electrical switch operatively coupled to the foot-operated pedal; and
a sensor operably coupled to both the electrical switch and the RF signal generator, wherein when the foot-operated pedal is activated the electrical switch is activated responsive thereto, wherein activation of the electrical switch induces the sensor to generate a third signal that is received by the RF signal generator, the RF signal generator transmitting one of the first and second RF signals in response to receiving the third signal.

4. The system of claim 1, further comprising a selector switch operably coupled to the RF signal generator for selecting at least one of the first and second devices.

5. The system of claim 1, further comprising a voice-recognition computer operably communicating with the RF signal generator for selecting at least one of the first and second devices based on a voice command.

6. The system of claim 1, wherein the first device comprises a dental implement.

7. The system of claim 6, wherein the dental implement comprises at least one of an air abrasion unit, an electro-surgery unit, a cavitron unit, a piezo-ultrasonic unit, a diamond probe, an intra-oral video device, a water-pick device, a dental drill, and a water irrigator.

8. A method for remotely controlling at least one device, comprising:
transmitting a first RF signal in response to activation of a foot-operated pedal when a first device is selected, utilizing a RF signal generator, the first RF signal having a first address value associated with the first device;
transmitting a second RE signal in response to activation of the foot-operated pedal when a second device is selected, utilizing the RF signal generator, the second RF signal having a second address value associated with the second device;
receiving the first RF signal at a first RF receiver unit; and
controlling the first device when the first RF signal has the first address value, utilizing the first RF receiver unit.

9. The method of claim 8, further comprising:
receiving the second RF signal at a second RF receiver unit; and
controlling the second device when the second RF signal has the second address value, utilizing the second RF receiver unit.

10. The method of claim 8, wherein controlling the first device comprises receiving the first RF signal and actuating the first device when the first RF signal has the first address value.

11. The method of claim 8, wherein the first device comprises a dental implement.

12. The method of claim 11, wherein the dental implement comprises at least one of an air abrasion unit, an electro-surgery unit, a cavitron unit, a piezo-ultrasonic unit, a diamond probe, an intra-oral video device, a water-pick device, a dental drill, and a water irrigator.

13. The method of claim 8, further comprising selecting at least one of the first and second devices based on a voice command utilizing a voice-recognition computer operably communicating with the RF signal generator.

14. A system for remotely controlling at least one device, comprising:
an RF signal generator configured to transmit a first RF signal when a foot-operated pedal is activated and a first device is selected, the first RF signal having a first address value associated with the first device, the RF signal generator further configured to transmit a second RF signal when the foot-operated pedal is activated and a second device is selected, the second RF signal having a second address value associated with the second device;
a selector device operably coupled to the RF signal generator for selecting at least one of the first and second devices;
a first RF receiver unit configured to receive the first RF signal and to actuate the first device when the first RF signal has the first address value; and
a second RF receiver unit configured to receive the second RF signal and to actuate the second device when the second RF signal has the second address value.

15. The system of claim 14, wherein the selector device comprises a selector switch.

16. The system of claim 14, wherein the selector device comprises a voice-recognition computer operably communicating with the RF signal generator for selecting at least one of the first and second devices based on a voice command.

17. The system of claim 14, wherein the first device comprises a dental implement.

18. The system of claim 17, wherein the dental implement comprises at least one of an air abrasion unit, an electro-surgery unit, a cavitron unit, a piezo-ultrasonic unit, a diamond probe, an intra-oral video device, a water-pick device, a dental drill, and a water irrigator.

* * * * *